United States Patent
Han et al.

(10) Patent No.: US 9,448,310 B2
(45) Date of Patent: Sep. 20, 2016

(54) APPARATUS AND METHOD FOR SPECTRUM ESTIMATION

(71) Applicant: SAMSUNG ELECTRONICS CO., LTD., Suwon-si (KR)

(72) Inventors: Seok Min Han, Seongnam-si (KR); Dong Goo Kang, Suwon-si (KR); Young Hun Sung, Hwaseong-si (KR); Sung Hoon Kang, Suwon-si (KR); Jae Hyun Kwon, Hwaseong-si (KR); Sung Su Kim, Yongin-si (KR); Hyun Hwa Oh, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 403 days.

(21) Appl. No.: 13/890,657

(22) Filed: May 9, 2013

(65) Prior Publication Data

US 2014/0105364 A1    Apr. 17, 2014

(30) Foreign Application Priority Data

Oct. 16, 2012 (KR) .......................... 10-2012-0114901

(51) Int. Cl.
G01T 1/36 (2006.01)
A61B 6/00 (2006.01)
G01T 1/29 (2006.01)
G01N 23/087 (2006.01)

(52) U.S. Cl.
CPC ........... *G01T 1/2914* (2013.01); *A61B 6/4241* (2013.01); *A61B 6/482* (2013.01); *G01N 23/087* (2013.01); *G01T 1/36* (2013.01); *G01N 2223/423* (2013.01)

(58) Field of Classification Search
CPC .. A61B 6/4241; A61B 6/482; G01N 23/087; G01N 2223/423
See application file for complete search history.

(56) References Cited

U.S. PATENT DOCUMENTS

| | | | | |
|---|---|---|---|---|
| 5,677,536 A | * | 10/1997 | Vickers | G01T 1/1642 250/252.1 |
| 7,120,226 B2 | * | 10/2006 | Ledoux | G01N 23/223 250/307 |
| 7,409,042 B2 | * | 8/2008 | Bertozzi | G01N 23/20066 378/86 |
| 7,668,289 B2 | * | 2/2010 | Proksa | G01N 23/046 378/19 |
| 2004/0188624 A1 | * | 9/2004 | Wong | G01T 1/1642 250/363.09 |
| 2006/0188060 A1 | * | 8/2006 | Bertozzi | G01N 23/20066 378/57 |
| 2006/0193433 A1 | * | 8/2006 | Ledoux | G01N 23/223 378/57 |
| 2007/0143036 A1 | * | 6/2007 | Stratis | G01N 23/00 702/28 |

(Continued)

FOREIGN PATENT DOCUMENTS

| | | |
|---|---|---|
| KR | 1020090103354 A | 10/2009 |
| KR | 1020110055870 A | 5/2011 |

(Continued)

*Primary Examiner* — Thomas R Artman
(74) *Attorney, Agent, or Firm* — Sughrue Mion, PLLC

(57) ABSTRACT

Provided is an apparatus for spectrum estimation. The apparatus includes a threshold setter which sets at least one threshold in order to separate a spectrum into at least one energy bin; a reference value setter which sets one of the at least one threshold as a reference threshold; a threshold adjuster which adjusts the at least one threshold based on a predetermined condition; a comparer which compares the reference threshold with the adjusted threshold; and an output unit which outputs a spectrum in which the adjusted threshold is set, when a value which is determined based on the comparison result corresponds to a predetermined maximum value.

23 Claims, 12 Drawing Sheets

(56) References Cited

U.S. PATENT DOCUMENTS

| | | | |
|---|---|---|---|
| 2008/0205585 A1* | 8/2008 | Proksa | G01N 23/046 378/19 |
| 2009/0310736 A1 | 12/2009 | Ziegler et al. | |
| 2010/0202584 A1 | 8/2010 | Wang et al. | |
| 2010/0215230 A1 | 8/2010 | Bornefalk et al. | |
| 2011/0019891 A1 | 1/2011 | Puong et al. | |
| 2011/0243413 A1* | 10/2011 | Tkaczyk et al. | 382/131 |
| 2012/0087463 A1* | 4/2012 | Greenberg et al. | 378/5 |
| 2012/0288880 A1* | 11/2012 | Heinecke | G01N 33/92 435/7.92 |
| 2013/0079918 A1* | 3/2013 | Spencer | B07C 5/3416 700/223 |
| 2013/0108013 A1* | 5/2013 | Leng et al. | 378/19 |

FOREIGN PATENT DOCUMENTS

| | | |
|---|---|---|
| KR | 1020110059988 A | 6/2011 |
| KR | 1020110080532 A | 7/2011 |

* cited by examiner

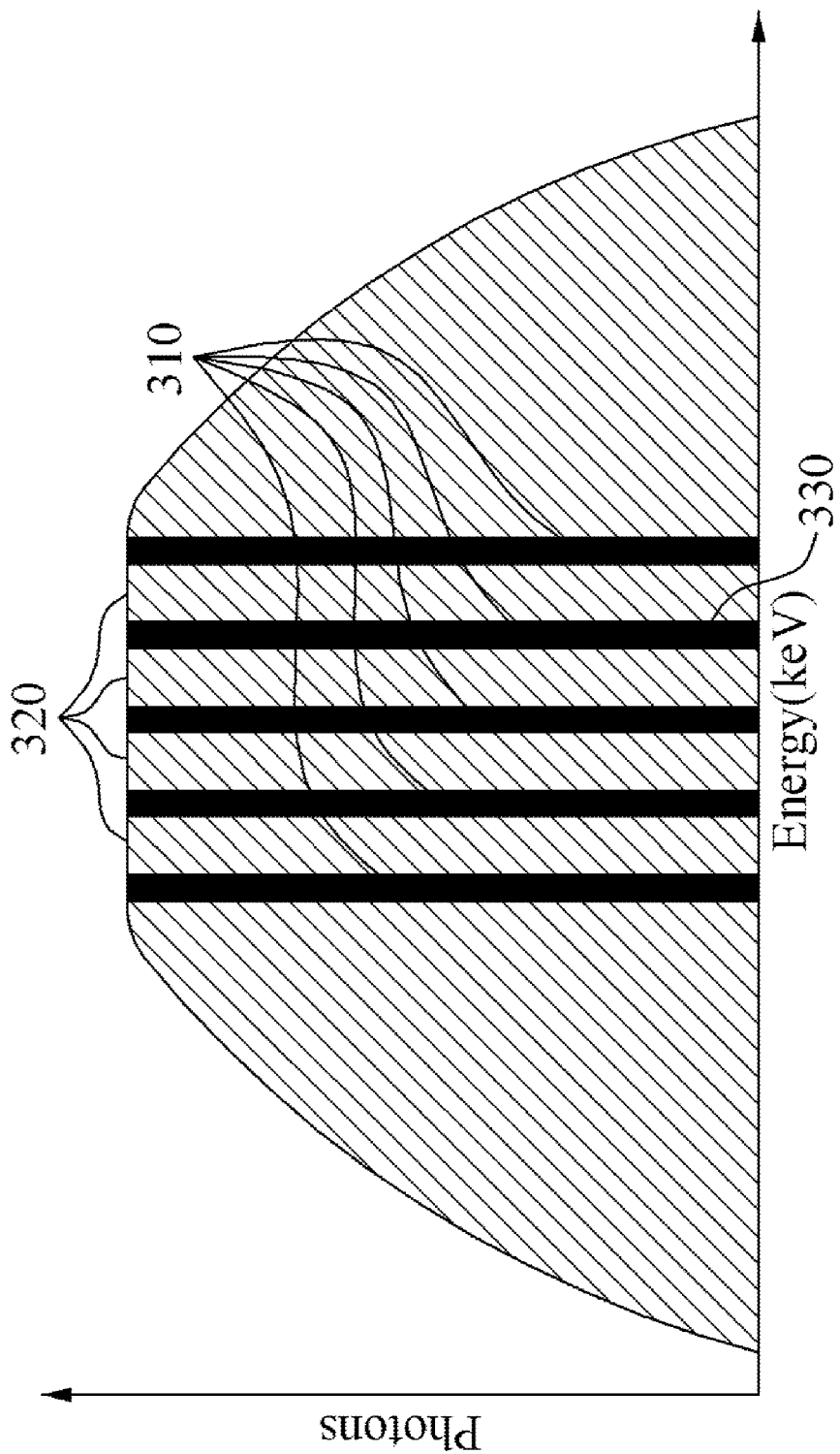

Low energy spectrum

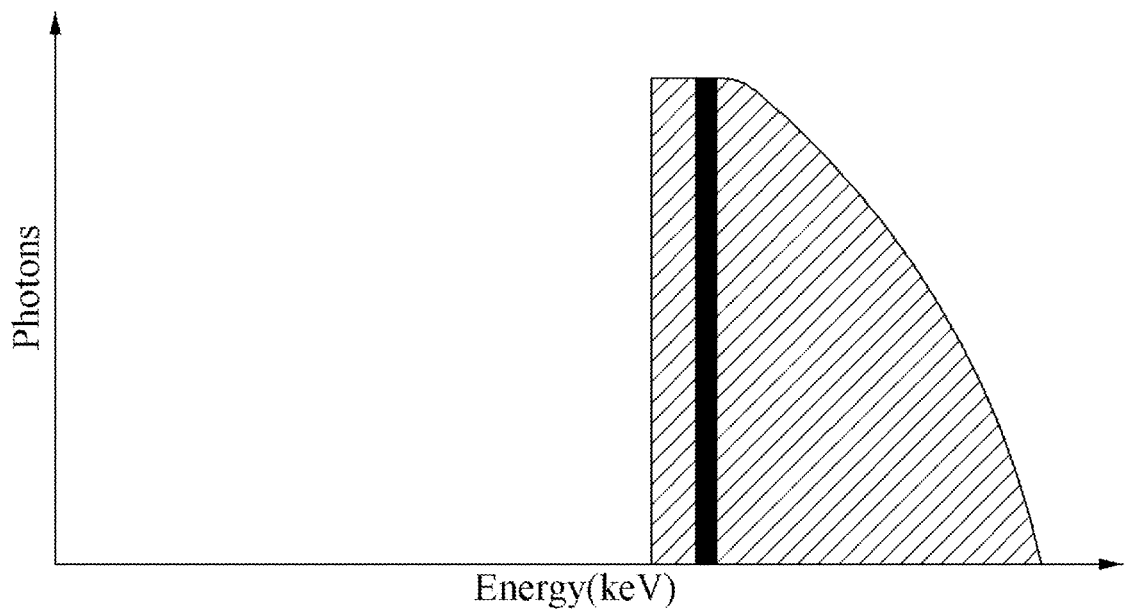

Low energy spectrum

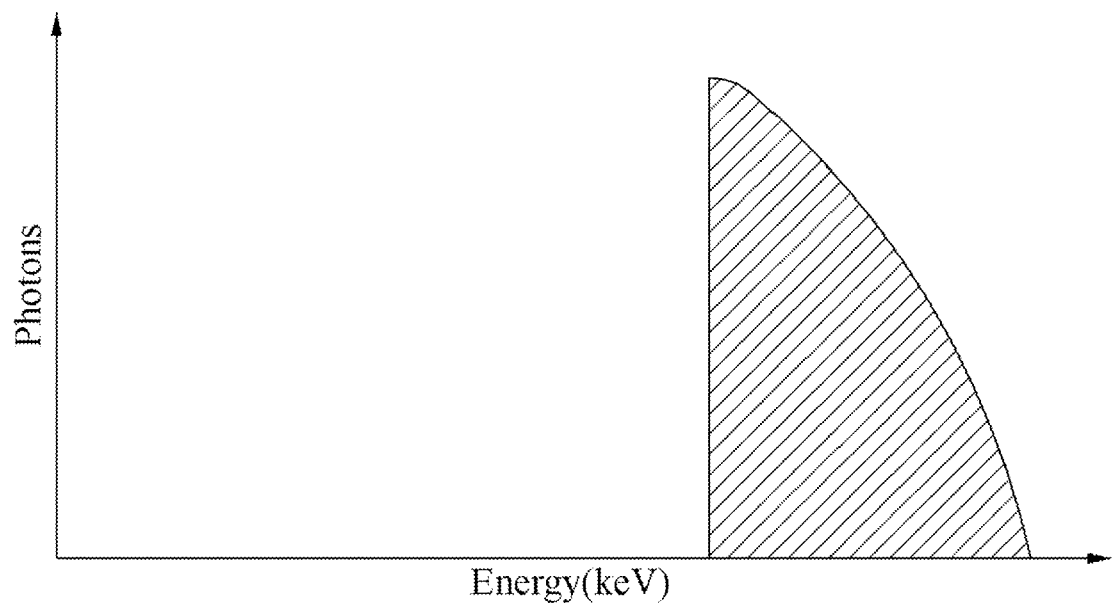

Low energy spectrum

High energy spectrum

Low energy spectrum

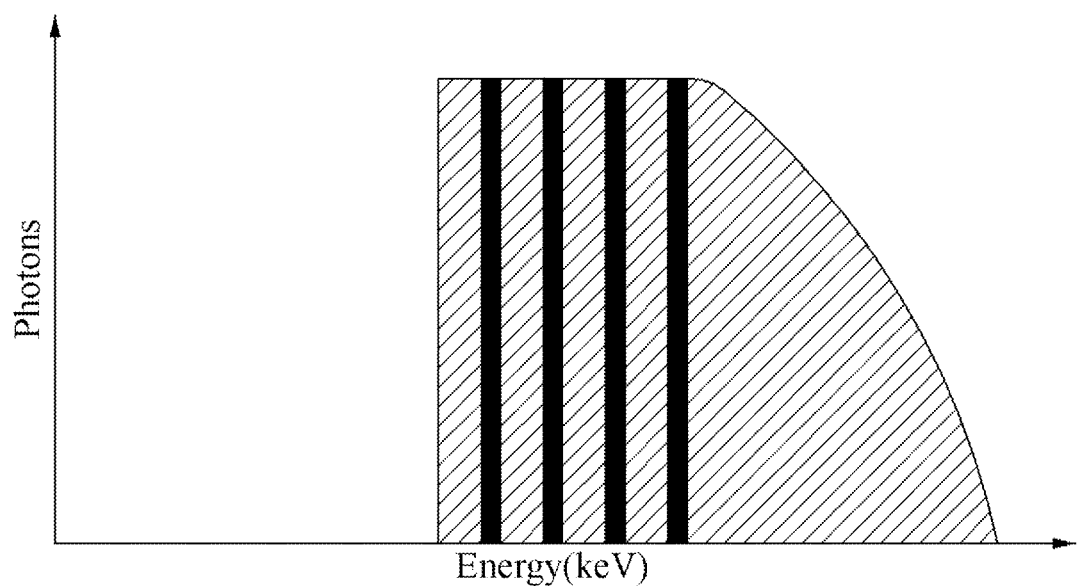

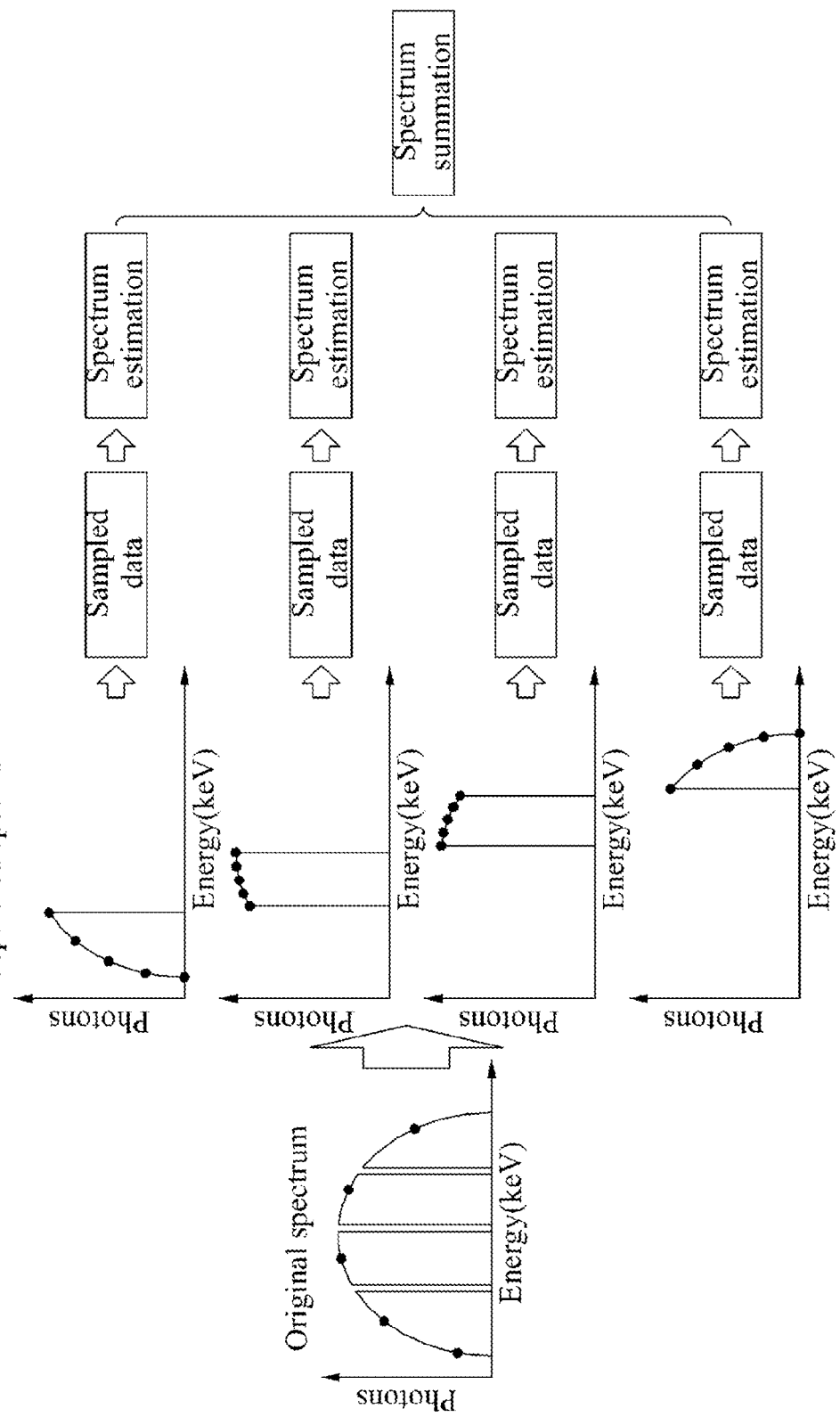

APPARATUS AND METHOD FOR SPECTRUM ESTIMATION

CROSS-REFERENCE TO RELATED APPLICATION

This application claims priority from Korean Patent Application No. 10-2012-0114901, filed on Oct. 16, 2012, in the Korean Intellectual Property Office, the disclosure of which is incorporated herein by reference in its entirety.

BACKGROUND

1. Field

Methods and apparatuses consistent with exemplary embodiments relate to an apparatus and method for separating an optimal spectrum and estimating a spectrum using a photon counting detector (PCD).

2. Description of the Related Art

Radiography using a multi-energy X-ray may be performed by adding a filter to a path via which an X-ray passes, or may be performed by adjusting an X-ray photographing condition, for example, tube voltage (kVp) and/or tube current (mAs), in order to optimize a photographing condition.

A photographing condition optimizing method using a photon counting detector (PCD), which is currently in development, may optimize a photographing condition by adjusting an interval between energy bins and a position of an energy bin.

A general photographing condition optimizing method may have some constraints in coping with a change in an optimal photographing condition which varies based on an object to be photographed.

In many cases, the general photographing condition optimizing method may perform optimization based on an approximate pattern of a component ratio of an imaging object to be photographed, or may perform individual optimization after photographing an X-ray image once.

SUMMARY

According to exemplary embodiments, there may be provided an apparatus for performing spectrum estimation, including: a threshold setter which sets at least one threshold in order to separate a spectrum into at least one energy bin; a reference value setter which sets one of the at least one threshold as a reference threshold; a threshold adjuster which adjusts the at least one threshold based on a predetermined condition; a comparer which compares the reference threshold with the adjusted at least one threshold; and an output unit which outputs a spectrum in which the adjusted at least one threshold is set, when a value which is determined based on a comparison result corresponds to a predetermined maximum value.

The threshold adjuster may finely adjust the at least one threshold when performing at least one of a multi-energy X-ray imaging operation and a dual energy X-ray imaging operation.

The predetermined condition may include at least one of a case in which a carrier to noise ratio (CNR) is a maximum, a case in which a detectability is a maximum, and a case in which noise is a minimum.

The threshold setter may set the at least one threshold by calculating a characteristic of a subject acquired from an image, and may separate at least one bin based on the set at least one threshold.

The reference threshold may be set based on at least one of a component, a thickness, and density of a subject.

The component of the subject may include a body constituent element which is selected from the group consisting of adipose tissue, glandular tissue, calcium, iodine, gold, and water.

The threshold adjuster may move at least one of the at least one energy bin in one of a low energy direction or a high energy direction.

A criterion relating to a determination of whether the at least one energy bin is moved in the low energy direction or the high energy direction may be determined based on the predetermined condition.

The spectrum estimation apparatus may further include: a combiner which estimates and entirety of the spectrum by combining the respective at least one energy bin.

According to exemplary embodiments, there may be provided a method for performing spectrum estimation, including: setting at least one threshold in order to separate a spectrum into at least one energy bin; setting one of the at least one threshold as a reference threshold; adjusting the at least one threshold based on a predetermined condition; comparing the reference threshold with the adjusted at least one threshold; and outputting a spectrum in which the adjusted at least one threshold is set, when a value which is determined based on a result of the comparing corresponds to a predetermined maximum value.

BRIEF DESCRIPTION OF THE DRAWINGS

The above and other aspects of exemplary embodiments will become apparent and more readily appreciated from the following detailed description of certain exemplary embodiments, taken in conjunction with the accompanying drawings of which:

FIG. 3 is a graph which illustrates a full energy spectrum of a photographed X-ray, according to one or more exemplary embodiments;

FIGS. 4A and 4B are graphs which illustrate an example of a spectrum separation which is optimized for a target A of an imaging object 1 by using at least one threshold which is set as a result of executing the method illustrated in FIG. 2;

FIGS. 5A and 5B are graphs which illustrate an example of a spectrum separation which is optimized for a target A of an imaging object 2 by using at least one threshold which is set as a result of executing the method illustrated in FIG. 2;

FIGS. 7A and 7B are graphs which illustrates an example of a spectrum separation which is optimized for a target B of an imaging object 2 by using at least one threshold which is set as a result of executing the method illustrated in FIG. 2; and FIG. 8 is a diagram which illustrates a process for estimating an energy bin spectrum through separation into a plurality of energy bins, according to one or more exemplary embodiments.

DETAILED DESCRIPTION

Figure 1:
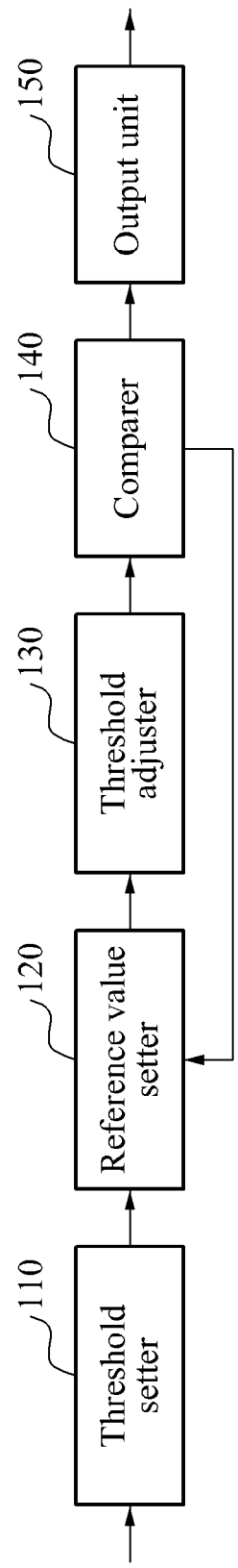
FIG. 1 is a block diagram which illustrates a spectrum estimation apparatus, according to one or more exemplary embodiments.

Reference will now be made in detail to exemplary embodiments, examples of which are illustrated in the accompanying drawings, wherein like reference numerals refer to the like elements throughout. Exemplary embodiments are described below in order to explain the present disclosure by referring to the figures.

Terminologies used in exemplary embodiments are used to appropriately describe the exemplary embodiments and thus, may be changed depending on a user, the intent of an operator, or a custom. Accordingly, the terminologies must be defined based on the following overall description of this specification.

FIG. 1 is a block diagram which illustrates a spectrum estimation apparatus, according to one or more exemplary embodiments.

Referring to FIG. 1, the spectrum estimation apparatus may include a threshold setter 110 which sets at least one threshold in order to separate a spectrum into at least one energy bin, a reference value setter 120 which sets one of the at least one threshold as a reference threshold, a threshold adjuster 130 which adjusts the at least one threshold based on a predetermined condition, a comparer 140 which compares the reference threshold with the adjusted at least one threshold, and an output unit 150 which outputs a spectrum in which the adjusted at least one threshold is set, when a value which is determined based on a comparison result corresponds to a predetermined maximum value.

Hereinafter, a method for estimating a spectrum by using the spectrum estimation apparatus will be described.

Figure 2:
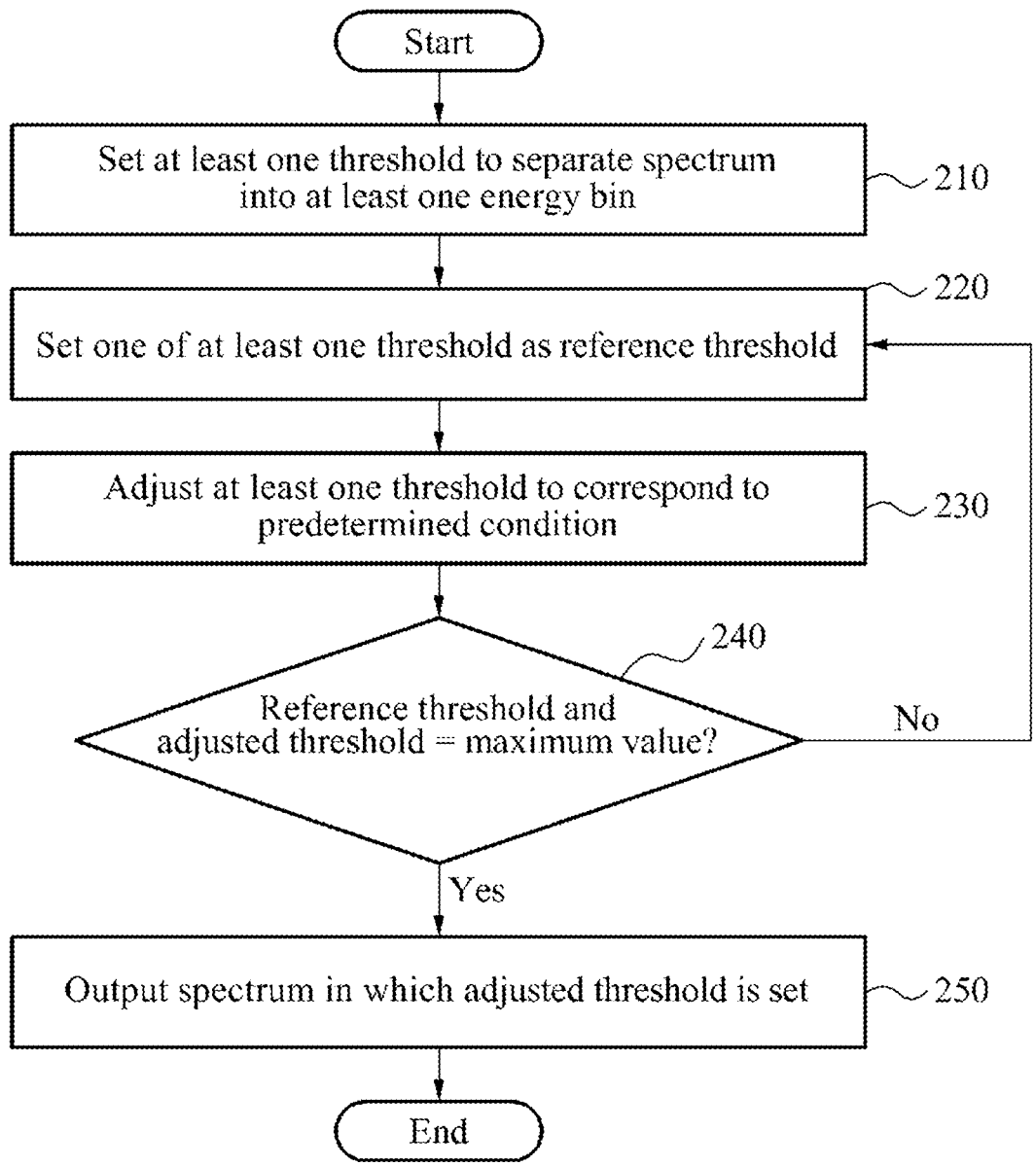
FIG. 2 is a flowchart which illustrates a spectrum estimation method, according to one or more exemplary embodiments.

FIG. 2 is a flowchart which illustrates a spectrum estimation method, according to one or more exemplary embodiments.

In operation 210, the spectrum estimation apparatus may set at least one threshold in order to separate a spectrum into at least one energy bin.

FIG. 3 is a graph which illustrates a full energy spectrum of a photographed X-ray, according to one or more exemplary embodiments.

Referring to FIG. 3, the spectrum estimation apparatus may set a plurality of thresholds 310 in order to separate a spectrum into a plurality of energy bins 320, and may set neighbor thresholds to be densely positioned about a reference threshold 330.

Referring again to FIG. 2, in operation 220, the spectrum estimation apparatus may set one of the at least one threshold as a reference threshold.

For example, the spectrum estimation apparatus may set, as the reference threshold, a predetermined threshold from among the plurality of densely positioned thresholds 310.

In operation 230, the spectrum estimation apparatus may adjust at least one threshold based on a predetermined condition.

In the case of performing a multi-energy X-ray imaging operation or a dual energy X-ray imaging operation, the threshold adjuster 130 may finely adjust the at least one threshold in order to achieve an optimal performance which is suitable for the condition.

The predetermined condition may include a case in which a carrier to noise ratio (CNR) is a maximum, a case in which a detectability is a maximum, and a case in which noise is a minimum.

In operation 240, the spectrum estimation apparatus may compare the reference threshold and the adjusted at least one threshold.

When a value which is determined based on a comparison result corresponds to a predetermined maximum value, the spectrum estimation apparatus may output a spectrum in which the adjusted at least one threshold is set in operation 250.

The threshold setter 110 may set the at least one threshold by calculating a characteristic of a subject acquired from an image, and may separate at least one bin based on the set at least one threshold.

The reference threshold may be set based on at least one of a component, a thickness, and density of a subject.

The component of the subject may include, for example, a k-edge material and a body constituent material, such as, for example, one of adipose tissue, glandular tissue, calcium, iodine, gold, and water.

The threshold adjuster 130 may move at least one of the at least one energy bin in one of a low energy direction and a high energy direction.

A criterion relating to a determination of whether the at least one energy bin is moved in the low energy direction or the high energy direction may be determined based on the predetermined condition.

The spectrum estimation apparatus may configure an optimal spectrum by moving a plurality of energy bins in one of the lower energy direction and the high energy direction, depending on necessity.

Figure 4A:
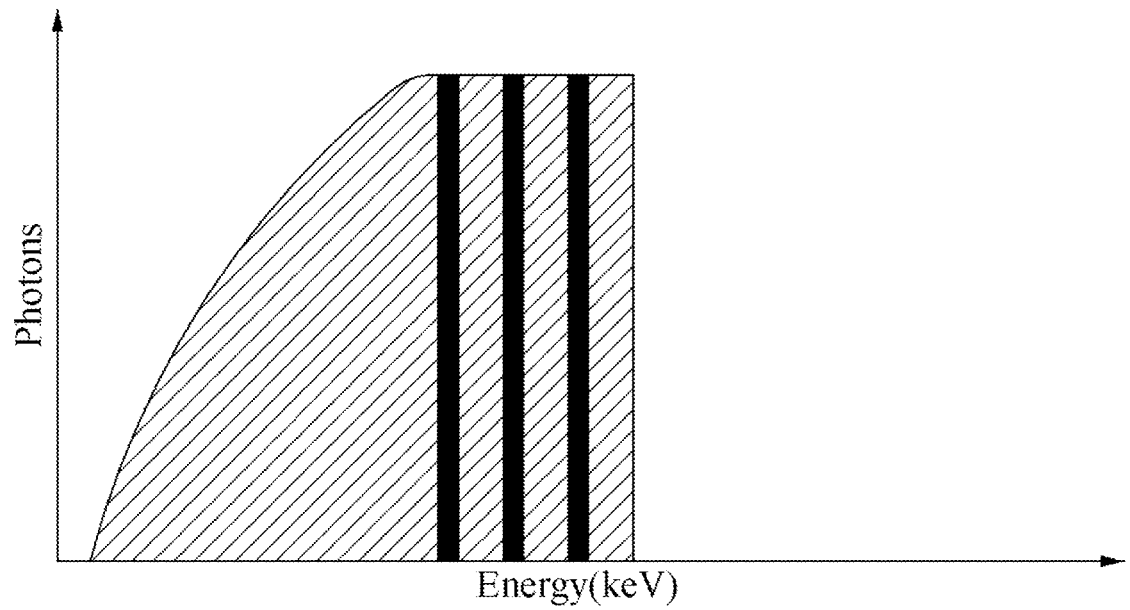

FIGS. 4A and 4B are graphs which illustrate an example of a spectrum separation which is optimized for a target A of an imaging object 1 by using at least one threshold which is set as a result of executing the method illustrated in FIG. 2.

Figure 5A:
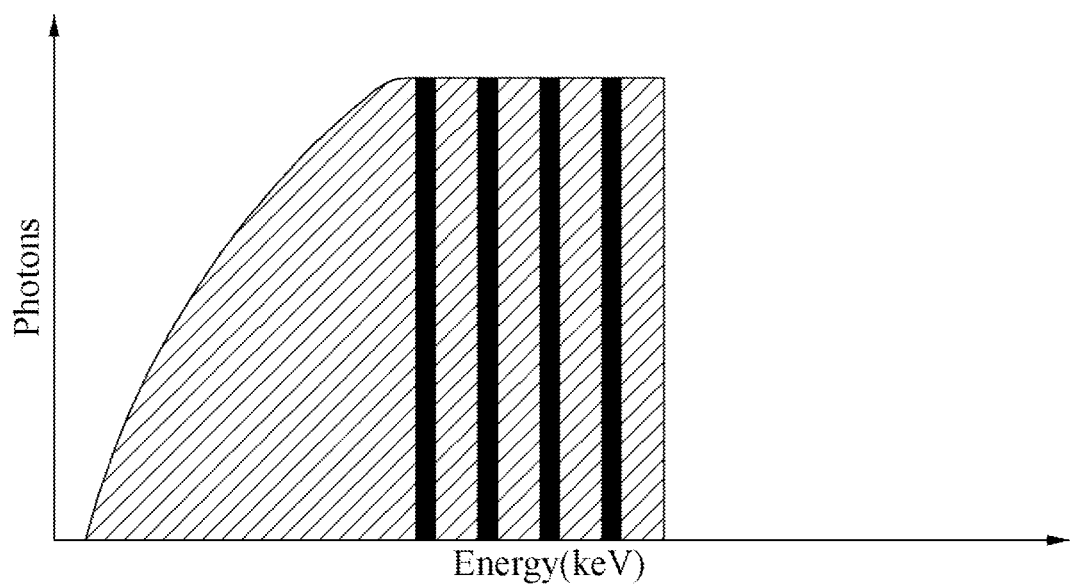

FIGS. 5A and 5B are graphs which illustrate an example of a spectrum separation which is optimized for a target A of an imaging object 2 by using at least one threshold which is set as a result of executing the method illustrated in FIG. 2.

For example, the spectrum estimation apparatus may move one of the plurality of energy bins of FIGS. 4A and 4B from a high energy portion of the energy spectrum to a low energy portion of the energy spectrum as illustrated in FIGS. 5A and 5B.

Figure 6A:
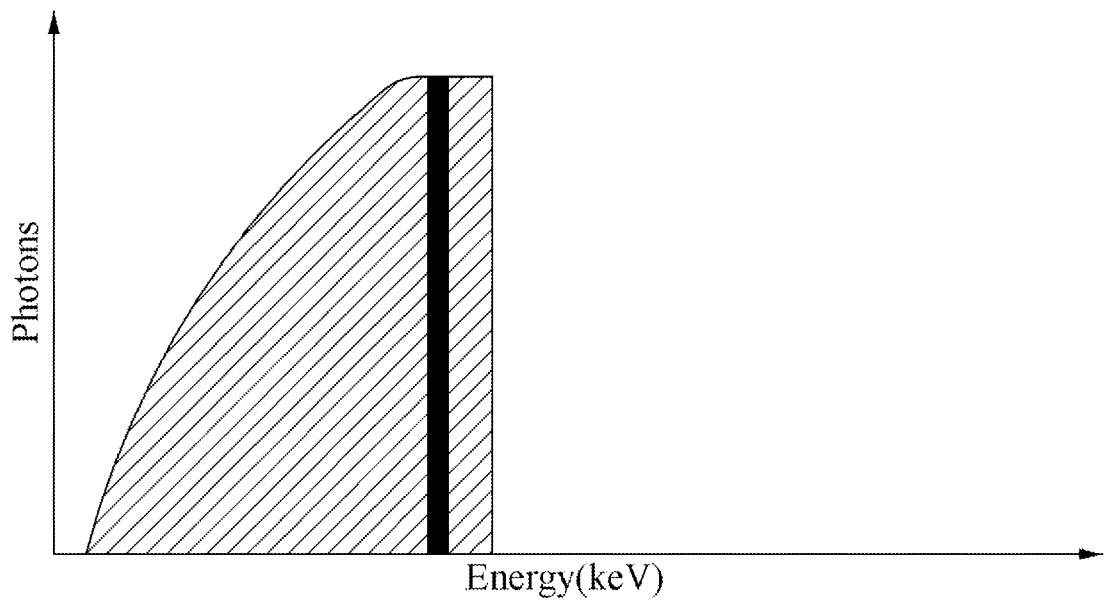
FIGS. 6A and 6B are graphs which illustrates an example of a spectrum separation which is optimized for a target B of an imaging object 1 by using at least one threshold which is set as a result of executing the method illustrated in FIG. 2.
Figure 6B:
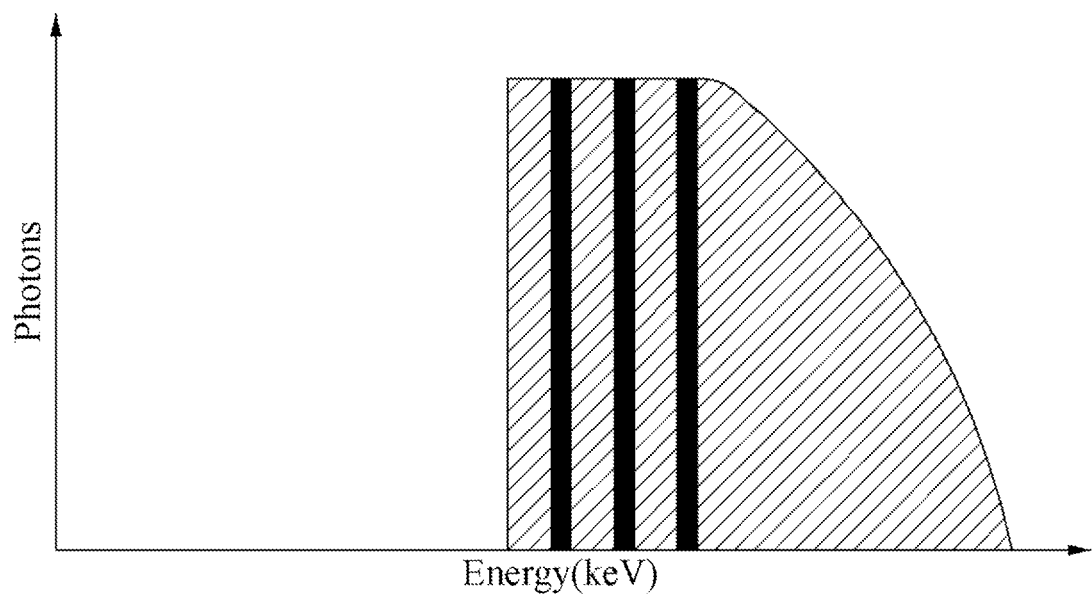

FIGS. 6A and 6B are graphs which illustrate an example of a spectrum separation which is optimized for a target B of an imaging object 1 by using at least one threshold which is set as a result of executing the method illustrated in FIG. 2.

Figure 7A:
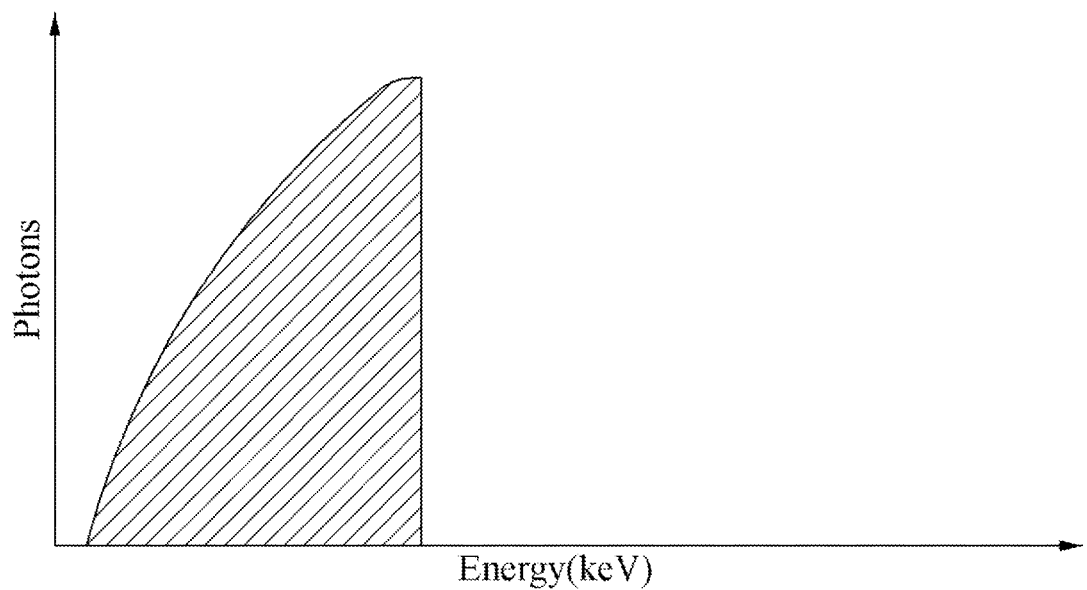

FIGS. 7A and 7B are graphs which illustrate an example of a spectrum separation which is optimized for a target B of an imaging object 2 by using at least one threshold which is set as a result of executing the method illustrated in FIG. 2.

For example, the spectrum estimation apparatus may move one of the plurality of energy bins of FIGS. 6A and 6B from a low energy portion of the energy spectrum to a high energy portion of the energy spectrum as illustrated in FIGS. 7A and 7B.

In particular, the high energy portion of the energy spectrum and the low energy portion of the energy spectrum may be separated for ease of description and thus, the spectrum may be separated into a greater number of energy bins based on the condition.

FIG. 8 is a diagram which illustrates a process for estimating an energy bin spectrum through separation into a plurality of energy bins, according to one or more exemplary embodiments.

Referring to FIG. 8, the full spectrum may be estimated by combining the respective energy bins by using a combiner (not shown).

The spectrum estimation apparatus may separate an X-ray spectrum into a plurality of energy bins, and may estimate each energy bin spectrum by applying spectrum sampling to each of the plurality of energy bins.

The spectrum estimation apparatus may estimate the full spectrum by combining the results of the respective energy bins.

In the case of setting an energy bin using a photon counting detector (PCD), the spectrum estimation apparatus may determine that an area excluding the set energy bin is "zero". Accordingly, the spectrum estimation apparatus may perform highly accurate estimation by narrowing the range of a sampling point.

The spectrum estimation apparatus may generate an auxiliary energy bin by setting a plurality of energy bin thresholds to be proximal with respect to a reference threshold, and may finely adjust an optimal energy bin threshold by combining or separating the auxiliary energy bin based on the predetermined condition.

The spectrum estimation apparatus may estimate an optimal spectrum photographing condition by setting an optimal energy threshold value instead of performing a photographing operation a plurality of times.

The spectrum estimation apparatus may accurately estimate an X-ray spectrum which is emitted from a source.

The spectrum estimation apparatus may set an optimal threshold which is suitable for an imaging object or a condition by using a one-time photographing operation, instead of performing X-ray imaging in advance, and may estimate an output value.

The spectrum estimation method according to the above-described exemplary embodiments may be recorded in transitory or non-transitory computer-readable media which include program instructions which implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as compact disk-read-only memory (CD ROM) disks and digital versatile disks (DVDs); magneto-optical media such as optical disks; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described exemplary embodiments, or vice versa.

Although a few exemplary embodiments have been shown and described, the present inventive concept is not limited thereto. Instead, it will be appreciated by those skilled in the art that changes may be made to these exemplary embodiments without departing from the principles and spirit of the disclosure, the scope of which is defined by the claims and their equivalents.

What is claimed is:

1. An apparatus for performing spectrum estimation, comprising:
   a photon counting detector (PCD) which counts a number of detected photons; and
   a processor configured to:
   set, based at least in part on an output received from the PCD, at least one threshold in order to separate a spectrum into at least one energy bin;
   set one of the at least one threshold as a reference threshold;
   adjust the at least one threshold based on a predetermined condition;
   compare the reference threshold with the adjusted at least one threshold, to generate a comparison result; and
   output a spectrum in which the adjusted at least one threshold is set, when a value which is determined based on the comparison result corresponds to a predetermined maximum value.

2. The apparatus of claim 1, wherein the processor is further configured to adjust the at least one threshold when performing at least one from among a multi-energy X-ray imaging operation which is based on at least three energy bins and a dual energy X-ray imaging operation which is based on two energy bins.

3. The apparatus of claim 1, wherein the predetermined condition comprises at least one from among a case in which a carrier to noise ratio (CNR) is a maximum, a case in which a detectability is a maximum, and a case in which noise is a minimum.

4. The apparatus of claim 1, wherein the processor is further configured to set the at least one threshold by calculating a characteristic of a subject acquired from an image, and to separate at least one bin based on the set at least one threshold.

5. The apparatus of claim 1, wherein the reference threshold is set based on at least one from among a component, a thickness, and density of a subject.

6. The apparatus of claim 5, wherein the component of the subject comprises a body constituent material which is selected from among adipose tissue, glandular tissue, calcium, iodine, gold, and water.

7. The apparatus of claim 1, wherein the processor is further configured to move at least one from among the at least one energy bin in one of a low energy direction and a high energy direction.

8. The apparatus of claim 7, wherein a criterion relating to a determination of whether the at least one energy bin is moved in the low energy direction or the high energy direction is determined based on the predetermined condition.

9. The apparatus of claim 1, wherein the at least one energy bin includes at least two energy bins, and the processor is further configured to:
   estimate an entirety of the spectrum by combining the respective at least two energy bins.

10. A method for performing spectrum estimation, comprising:
    counting, by a photon counting detector (PCD), a number of detected photons;
    setting, based at least in part on an output received from the PCD, at least one threshold in order to separate a spectrum into at least one energy bin;
    setting one of the at least one threshold as a reference threshold;

adjusting the at least one threshold based on a predetermined condition;
comparing the reference threshold with the adjusted at least one threshold; and
outputting a spectrum in which the adjusted at least one threshold is set, when a value which is determined based on a result of the comparing corresponds to a predetermined maximum value.

11. The method of claim 10, wherein the adjusting of the at least one threshold comprises adjusting the at least one threshold when performing at least one from among a multi-energy X-ray imaging operation which is based on at least three energy bins and a dual energy X-ray imaging operation which is based on two energy bins.

12. The method of claim 10, wherein the predetermined condition comprises at least one from among a case in which a carrier to noise ratio (CNR) is a maximum, a case in which a detectability is a maximum, and a case in which noise is a minimum.

13. The method of claim 10, wherein the setting of the at least one threshold comprises:
setting the at least one threshold by calculating a characteristic of a subject acquired from an image; and
separating at least one bin based on the set at least one threshold.

14. The method of claim 10, wherein the reference threshold is set based on at least one of a component, a thickness, and density of a subject.

15. The method of claim 14, wherein the component of the subject comprises a body constituent material which is selected from among adipose tissue, glandular tissue, calcium, iodine, gold, and water.

16. The method of claim 10, wherein the adjusting of the at least one threshold comprises moving at least one from among the at least one energy bin in one of a low energy direction and a high energy direction.

17. The method of claim 16, wherein a criterion relating to a determination of whether the at least one energy bin is moved in the low energy direction or the high energy direction is determined based on the predetermined condition.

18. The method of claim 10, wherein the at least one energy bin includes at least two energy bins, and the method further comprising:
estimating an entirety of the spectrum by combining the respective at least two energy bins.

19. A non-transitory computer-readable recording medium which stores a program which executes the method of claim 10.

20. A spectrum estimation apparatus, comprising:
a photon counting detector (PCD) which counts a number of detected photons; and
a processor configured to:
set, based at least in part on an output received from the PCD, a first energy value as a reference threshold and separates at least one energy bin with respect to the reference threshold;
output an energy spectrum which corresponds to the separated at least one energy bin when a value which is determined based on an amount of energy in the at least one energy bin corresponds to a predetermined maximum value; and
adjust an amount of energy in the at least one energy bin based on a predetermined condition.

21. The spectrum estimation apparatus of claim 20, wherein the predetermined condition comprises at least one from among a case in which a carrier to noise ratio (CNR) is a maximum, a case in which a detectability is a maximum, and a case in which noise is a minimum.

22. The spectrum estimation apparatus of claim 20, wherein the reference threshold is set based on at least one from among a k-edge material of a subject, a body constituent material of the subject, a thickness of the subject, and a density of the subject.

23. The spectrum estimation apparatus of claim 22, wherein the body constituent material is selected from among adipose tissue, glandular tissue, calcium, iodine, gold, and water.

* * * * *